United States Patent

Dann

[11] Patent Number: 5,630,429
[45] Date of Patent: May 20, 1997

[54] MALE INCONTINENCE DEVICE

[75] Inventor: Jeffrey A. Dann, Worcester, Mass.

[73] Assignee: NEBL, Inc., Worcester, Mass.

[21] Appl. No.: 540,896

[22] Filed: Oct. 11, 1995

[51] Int. Cl.$^6$ ...................................................... A61F 5/48
[52] U.S. Cl. ................................. 128/885; 128/DIG. 25; 604/349
[58] Field of Search ................................. 128/846, 885, 128/886, 849–856, 842, 844, 918; 604/349–356; 600/29–31

[56] References Cited

U.S. PATENT DOCUMENTS

| | | | |
|---|---|---|---|
| 4,652,259 | 3/1987 | O'Neil | 604/54 |
| 4,710,169 | 12/1987 | Christopher | 128/DIG. 25 |
| 4,963,137 | 10/1990 | Heyden | 604/349 |
| 5,074,314 | 12/1991 | Wilson | 604/349 |
| 5,195,998 | 3/1993 | Abraham | 604/349 |
| 5,242,391 | 9/1993 | Place et al. | 604/60 |
| 5,306,226 | 4/1994 | Suluma | 128/DIG. 25 |
| 5,334,175 | 8/1994 | Conway et al. | 604/352 |
| 5,366,449 | 11/1994 | Gilberg | 604/349 |
| 5,380,312 | 1/1995 | Goulter | 604/352 |
| 5,409,475 | 4/1995 | Steer | 604/353 |
| 5,415,179 | 5/1995 | Mendoza | 128/842 |
| 5,417,666 | 5/1995 | Coulter | 604/349 |
| 5,445,626 | 8/1995 | Gigante | 604/349 |

OTHER PUBLICATIONS

Article entitled "Bardex I.C. –Foley Catheter", Bard Urological Division, C.R. Bard, Inc. (Date Unknown –Not admitted to be prior art).

Article entitled "Bard Cunningham Incontinenace Clamp", Bard Patient Care Division, C.R. Bard, Inc. (Date Unknown –Not admitted to be prior art).

*Primary Examiner*—Michael A. Brown
*Attorney, Agent, or Firm*—Judith C. Crowley; Nutter, McClennen & Fish

[57] ABSTRACT

A device for preventing male urinary incontinence is provided having a sheath and a protuberance. The sheath is sized to cover at least a portion of the glans penis of a user. The protuberance, which extends from the sheath, is sized and shaped to fit into the urethra of the user. The protuberance forms a cavity, which receives a plug. Adhesive may be disposed on the sheath to adhere it to the glans penis of the user.

15 Claims, 4 Drawing Sheets

5,630,429

MALE INCONTINENCE DEVICE

FIELD OF THE INVENTION

The present invention relates to devices for preventing male urinary incontinence and, in particular, to male incontinence devices which occlude the meatus urinarius.

BACKGROUND OF THE INVENTION

Male urinary incontinence can result from a variety of physical or mental dysfunctions. Radical prostatectomies, complications arising from open or transurethral prostatectomy, and trauma to the membranous urethra or bladder neck can all cause permanent or temporary incontinence in men. Neurogenic bladder dysfunction or benign prostatic hyperplasia can also cause urinary incontinence.

Male urinary incontinence affects more than two million men, and no completely reliable or acceptable surgical means exists for correction. Thus far, males wishing to prevent involuntary urine leakage have been relegated to one of two solutions: catheter-type collection devices or crude clamping means.

Several disadvantages exist with catheter-type devices. Such devices can easily leak, are often difficult to put on, and can be uncomfortable to wear and embarrassing to empty. Large urine spills result if the device slips off.

Clamping devices have other difficulties associated with them. In particular, such devices can cut off circulation to the glans, requiring the user to remove the clamp several times daily in order to allow proper blood flow. In addition to the pressure, the size and weight of these devices make them extremely uncomfortable to wear. Additionally, these devices do not always provide sufficient pressure to keep the urethra in a pinched or closed position because the corpus spongiosum is flexible, and allows the urethra some freedom of movement, even when clamped.

Therefore, it is important to provide a device that eliminates male incontinence, can be comfortably worn throughout the day, is easily applied and easily removed.

The present invention provides the aforementioned desirable characteristics while avoiding the undesirable characteristics of prior art devices.

SUMMARY OF THE INVENTION

A male incontinence device is provided which has a sheath and a protuberance. The sheath is sized to cover at least a portion of the glans penis of a user. The protuberance, which extends from the sheath, is sized and shaped to fit into the urethra. This device allows the meatus urinarius to be effectively and simply occluded to protect against urine leakage.

In other embodiments, the sheath has a conical shape, a hemispherical shape, or is form-fitted to the glans penis. The sheath may be constructed of an elastomeric material, such as elastomeric urethanes, polyvinylchloride, silicone, thermoplastics or synthetic polymeric material. In another embodiment the surface of the sheath that contacts the glans penis of the wearer has an adhesive disposed thereon. In yet another embodiment, the protuberance forms a hollow for receiving a plug. The plug can be conical in shape, formed of resilient material, or a screw-type device which allows the diameter of the plug to be increased or decreased by turning the screw. In another embodiment the protuberance defines a bore and the bore is fitted with a valve.

DETAILED DESCRIPTION OF THE INVENTION

Referring now to FIGS. 1A, 1B, 2A, 2B, 3A, and 3B, a male incontinence device 10, as shown in top plan view and perspective view in respective Figures, has a sheath 12, 14 or 16 and a hollow protuberance 18 defining a cavity 22. Protuberance 18 is sized and shaped to fit into the urethra of the user, thereby occluding the meatus urinarius and preventing urine leakage. Protuberance 18 may be made of any rigid or resilient material that is suitable for insertion into the urethra and have a diameter and length which effectively occludes the meatus urinarius while avoiding user discomfort.

Figure 1A:
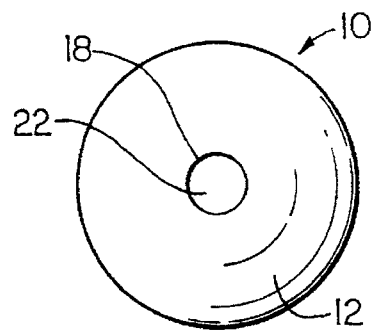
FIG. 1A is a front plan view of an embodiment of a male incontinence device having a hemispherical sheath and a hollow protuberance.
Figure 1B:
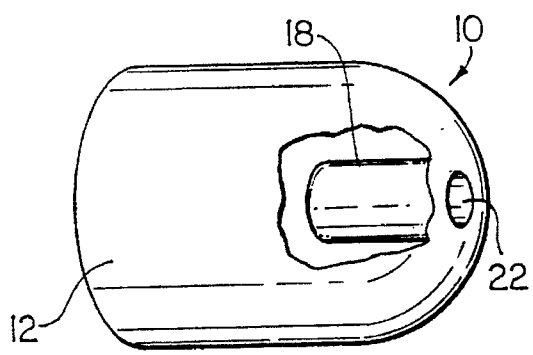
FIG. 1B is a perspective view of the male incontinence device of FIG. 1A.
Figure 2A:
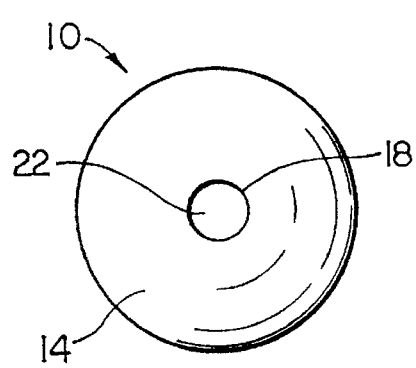
FIG. 2A is a front plan view of an embodiment of a male incontinence device having a conical sheath and a hollow protuberance.
Figure 2B:
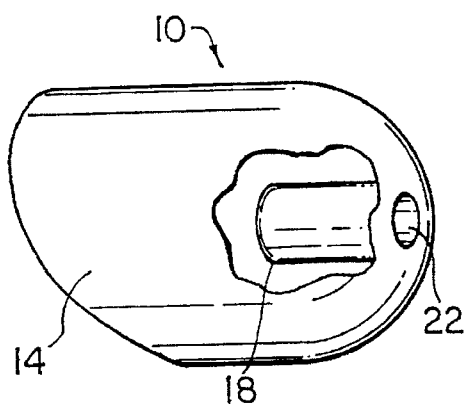
FIG. 2B is a perspective view of the male incontinence device of FIG. 2A.
Figure 3A:
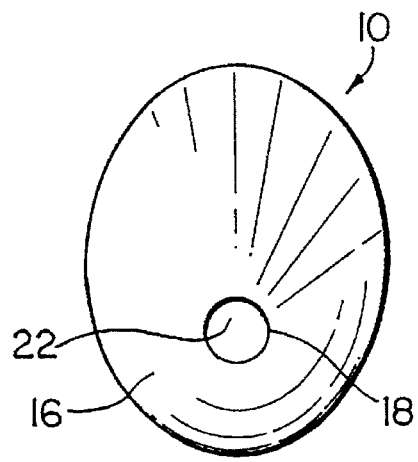
FIG. 3A is a front plan view of an embodiment of a male incontinence device having a form-fitted sheath and a hollow protuberance.
Figure 3B:
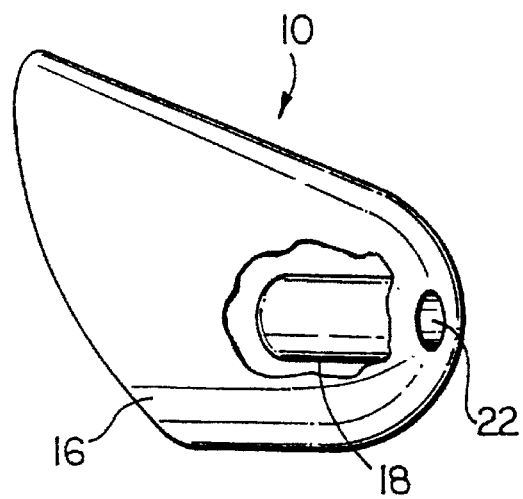
FIG. 3B is a perspective view of the male incontinence device of FIG. 3A.

Sheath 12, 14 or 16 may be any size or shape, provided that it covers at least a portion of the glans penis of the user. FIGS. 1A and 1B show sheath 12 having a substantially hemispherical shape. FIGS. 2A and 2B show sheath 14 having a substantially conical shape. FIGS. 3A and 3B show sheath 16 having a shape that is form fitted to the glans penis of the user. In one embodiment, sheath 12 is a condom-like device which unrolls to cover the entire penile shaft. However, sheath 16, which covers the entire glans penis of the user, is preferred. Sheath 12, 14 or 16 provides a seal to the glans penis which secures protuberances 18 in the meatus and provides additional protection against urine leakage. Sheath 12, 14 or 16 may be made of any rubbery or flexible material, preferably of an elastomeric urethane or thermoplastic. Any material will suffice provided that it is durable and waterproof. Preferably the medical grade thermoplastic elastomer utilizes shore-A 30–80 durometer grade material. It is preferable for sheath 12, 14 or 16 and protuberance 18 to be formed of the same unitary piece of material, but separate pieces of material could be used as long as a waterproof seam between sheath 12, 14 or 16 and protuberance 18 or 20 is provided.

Figure 4A:
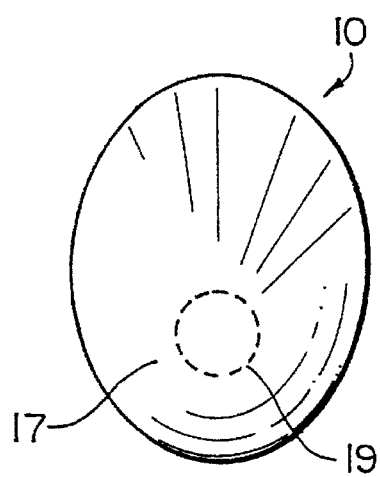
FIG. 4A is a front plan view of an embodiment of a male incontinence device having a form-fitted sheath and a solid protuberance.
Figure 4B:
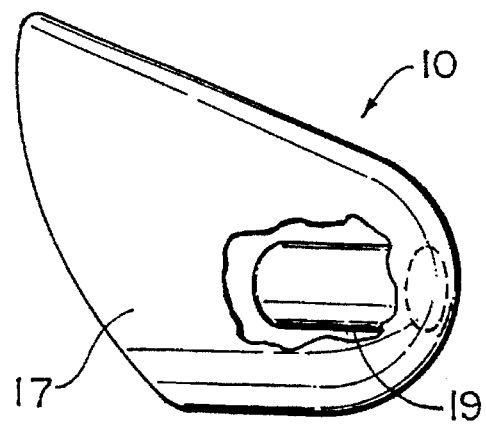
FIG. 4B is a perspective view of the male incontinence device of FIG. 4A.

FIGS. 4A and 4B show a male incontinence device 10 in top plan view and perspective view, having a sheath 17 and a solid protuberance 19, shown in phantom. Protuberance 19 is sized and shaped to fit into the urethra of the user, thereby occluding the meatus urinarius and preventing urine leakage. Protuberance 19 may be made of any rigid or resilient material that is suitable for insertion into the urethra and have a diameter and length which effectively occludes the meatus urinarius while avoiding user discomfort. Sheath 17 is substantially similar to sheaths 12, 14 and 16 which are described above, although minor modifications may be made in order to accommodate solid protuberance 19 during the manufacturing process.

Figure 5:
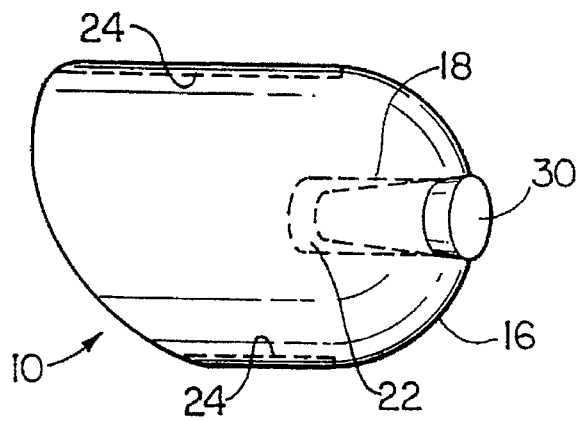
FIG. 5 is a perspective view of the male incontinence device of FIG. 2A showing a conical plug inserted into the hollow protuberance.

FIG. 5 shows adhesive 24 disposed on the inner surface of sheath 16. Adhesive 24 may be used in order to more securely fasten sheath 16 to the glans penis. Adhesive 24 can be applied by the user when application of device 10 is desired, or adhesive 24 may be manufactured onto sheath 16. Any medical grade adhesive may be used, provided that enough is used to securely fasten sheath 16 to glans penis while allowing device 10 to be removed without causing discomfort. In one embodiment, adhesive 24 is a strip of material having adhesive on both sides.

FIG. 5 shows a male incontinence device 10 having a hollow protuberance 18 and a plug 30 inserted into cavity 22. Plug 30 is positioned into the cavity 22 from outside the sheath 16 in order to force the walls of the protuberance 18 against the walls of the meatal mucosa in order to better prevent urine leakage.

Figure 6:
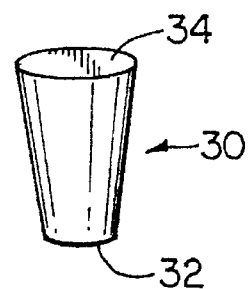
FIG. 6 is a perspective view of the conical plug of FIG. 5.

Plug 30 may take any number of forms, so long as protuberance 18 is pressed against the walls of the meatal mucosa. FIG. 6 shows a truncated conical plug 30. Smaller end 32 of plug 30 is preferably size 14 french while larger end 34 is preferably size 22 french. It is noted, however, that any range of measurements may be used, keeping in mind that conical plug 30 should taper so that it is easily inserted into the urethra yet be capable of effectively occluding the meatus urinarius upon further insertion. Plug 30 may be constructed of any material provided it is rigid enough to be inserted into protuberance 18, preferably plastic is used.

Figure 7A:
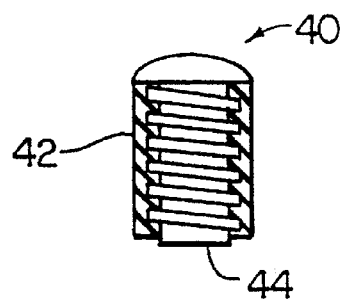
FIG. 7A is a side view of an embodiment of a screw-type plug in a compressed configuration.
Figure 7B:
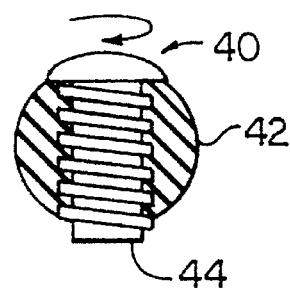
FIG. 7B is a side view of the screw-type plug of FIG. 7A in an expanded configuration.

FIG. 7A shows a compressed screw-type plug 40. Plug 40 is provided with a flexible covering 42, which expands in diameter when the screw 44 is turned. FIG. 7B shows plug 40 after screw 44 has been turned and its diameter is expanded. Flexible covering 42 can be formed of any flexible material, and screw 44 can be any material, although plastic is preferred. The size of this plug, when compressed and when expanded may vary, so long as when compressed, the plug easily fits into the urethra and when expanded it effectively occludes the meatus urinarius.

Figure 8A:
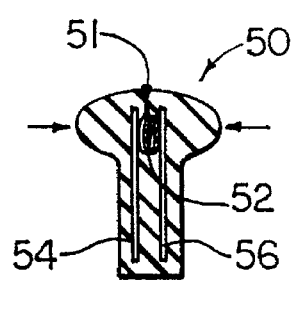
FIG. 8A is a side view of an embodiment of a compression-type plug, made from resilient material, in a compressed configuration.
Figure 8B:
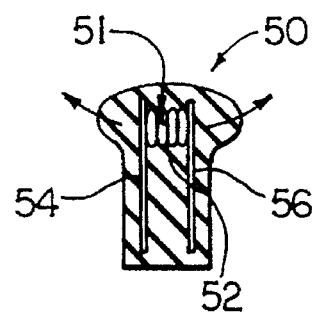
FIG. 8B is a side view of the compression-type plug of FIG. 8A, in an expanded configuration.

FIG. 8A shows a plug 50 made of resilient material and containing a spring assembly 51. It is preferred that the material used for plug 50 is resilient enough that plug 50 and spring assembly 51 can be compressed by light hand pressure. The spring assembly 51 has a spring 52 and bars 54 and 56 disposed inside the resilient material. When pressure is applied to the plug, bar 54 and 56 transfer the compression force to spring 52 and the plug is compressed. As shown in FIG. 8B, when pressure is released spring 52 resumes its former size and expands the plug. Although spring 52 and bars 54 and 56 are shown, any mechanism for expanding and compressing plug 50 is suitable. The size of this plug, when compressed and when expanded may vary, so long as when compressed, the plug easily fits into the urethra and when expanded it effectively occludes the meatus urinarius. Plug 50 can be made of any suitable flexible material such as plastic or rubber.

Figure 9A:
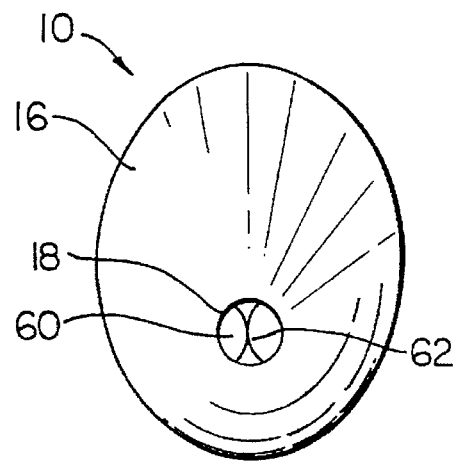
FIG. 9A is a front plan view of an embodiment of a male incontinence device having a form-fitted sheath and showing a bore and valve.
Figure 9B:
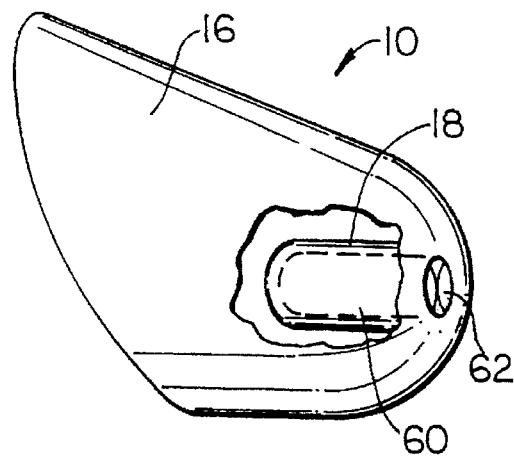
FIG. 9B is a perspective view of the male incontinence device of FIG. 9A.

FIGS. 9A and 9B show a male incontinence device 10 having a hollow protuberance 18 defining a bore 60 and having a valve 62 in the bore. The protuberance 18 is inserted into the urethra against the walls of the meatal mucosa to form a water tight seal between the walls of the urethra and the protuberance 18. The protuberance 18 can be rigid or can be forced against the walls of the meatal mucosa by the valve 62. Valve 62 allows urine to flow through it only when the valve 62 is open. Thus, when valve 62 is closed, the meatal urinarius is occluded and urine is prevented from leaking. Valve 62 may be of any construction which is easily opened and closed, and capable of withstanding typical bladder pressures. As above, sheath 16 may be any size and shape provided that sheath 16 covers at least a portion of the glans penis of the user.

Figure 10:
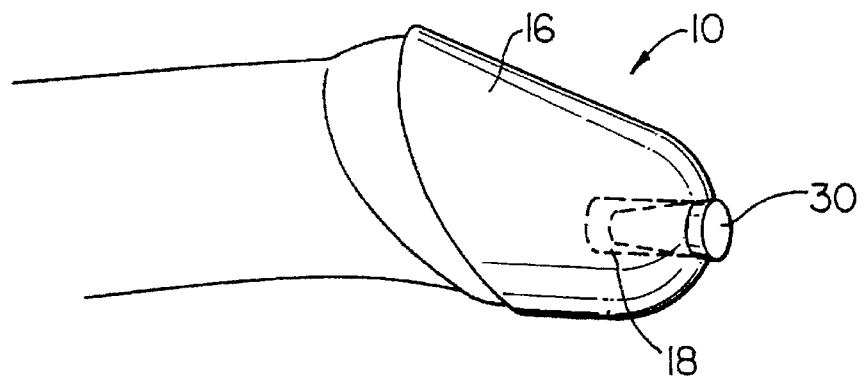
FIG. 10 is a perspective view of the male incontinence device of 3A in use.

FIG. 10 shows the male incontinence device of FIG. 3A in use, having the plug of FIG. 6 inserted. Using a device 10 made of flexible elastomeric material and having a hollow protuberance 18 is accomplished in the following manner. The user rolls sheath 16 back so that protuberance 18 is exposed. The user then inserts protuberance 18 into the urethra. Ideally, the meatus urinarius is firmly seated against sheath 16, although this is not strictly necessary. If adhesive 24 is not manufactured onto sheath 16 and is desired, the user applies it at this time. Adhesive 24 may be applied as an adhesive strip either to the surface of sheath 16 or directly to the glans penis. Sheath 16 is now restored to its original position, and now covers at least a portion of the glans penis. If plug 30 is desired, it is inserted now. Plug 30 is inserted into hollow protuberance 18 until the meatus urinarius is firmly occluded. When the user wishes to remove device 10, the user removes plug 30, rolls back sheath 16 from contact with the glans penis, and removes protuberance 18 from the urethra.

Although only preferred embodiments are specifically illustrated and described herein, it will be appreciated that many other modifications and variations of the present invention are possible in light of the above teachings and within the preview of the appended claims without departing from the spirit and intended scope of the invention. Other objects, features and advantages of the invention shall become apparent when the following drawings, description and claims are considered.

What is claimed is:

1. A device for preventing male urinary incontinence comprising:

a sheath, having an inner surface and an outer surface, sized to cover at least a portion of the glans penis of a user; and a protuberance, extending from said inner surface of said sheath, said protuberance sized and shaped to extend into and terminate in the urethra of the penis so as to occlude the urethra, wherein said protuberance defines a hollow.

2. The device of claim 1 further comprising a plug sized and shaped to fit into said hollow of said protuberance.

3. The device of claim 2 wherein said plug is substantially conical.

4. The device of claim 2 wherein said plug further includes a screw and a flexible covering, said flexible covering in a surrounding relation with said screw, wherein turning said screw causes said flexible covering to expand in diameter.

5. The device of claim 2 wherein said plug comprises a spring device covered by a resilient material.

6. A method for preventing male urinary incontinence using a device comprising a sheath, having an inner surface and an outer surface, sized to cover at least a portion of the glans penis of a user and a protuberance extending from said sheath and sized and shaped to extend into the urethra of a user, the method comprising the steps of:

occluding the meatus urinarius by inserting the protuberance into the urethra of the user; and securing the protuberance in the urethra by attaching the sheath to the glans penis of said user.

7. The method of claim 6 further comprising the steps of:

providing an adhesive; and disposing the adhesive on the inner surface of the sheath, such that the sheath adheres to the glans penis of the user.

8. A device for preventing male urinary incontinence comprising:

a sheath sized to cover at least a portion of the glans penis and having an inner surface and an outer surface;

a protuberance extending from said sheath and &fining a hollow, wherein said protuberance is size and shaped to extend into and terminate in the urethra of the penis; and a plug sized and shaped to fit into said hollow of said protuberance.

9. The device of claim 8 wherein said sheath further includes an adhesive disposed on said inner surface of said sheath.

10. The device of claim 8 wherein said sheath further includes a strip of material, having first and second sides, and including an adhesive disposed on said first and second sides, said material disposed on said inner surface of said sheath.

11. A device for preventing male urinary incontinence comprising:

a sheath, having an inner surface and an outer surface, sized to cover at least portion of the glans penis of a user; and a protuberance, extending from said inner surface of said sheath to terminate in the urethra of a user, said protuberance having a sheath end positioned at the meatus urinarius of the user and a urethra end sized and shaped to enter the urethra of the user, wherein said sheath end of said protuberance includes a valve.

12. The device of claim 11 wherein said sheath further includes an adhesive disposed on said inner surface of said sheath.

13. The device of claim 11 wherein said sheath further includes a strip of material, having first and second sides, and including an adhesive disposed on said first and second sides, said material disposed on said inner surface of said sheath.

14. The method of claim 6 further comprising the steps of:

providing a material having first and second sides and including adhesive disposed on the first and second sides of the material; and disposing the material on the inner surface of the sheath, such that the sheath adheres to the glans penis of the user.

15. The method of claim 6, wherein the protuberance defines a hollow, and further comprising the steps of:

providing a plug sized and shaped to fit into said hollow; and inserting said plug into said hollow.

* * * * *